United States Patent [19]

Takaki

[11] Patent Number: 5,064,831
[45] Date of Patent: Nov. 12, 1991

[54] NAPHTHOTHIOPHENIMINES FOR TREATING NEURONAL DISORDERS CAUSED BY ISCHEMIA

[75] Inventor: Katherine S. Takaki, Middletown, Conn.

[73] Assignee: Bristol-Myers Squibb Co., New York, N.Y.

[21] Appl. No.: 583,627

[22] Filed: Sep. 14, 1990

[51] Int. Cl.[5] .................. A61K 31/495; A61K 31/40; C07D 403/00; C07D 487/00
[52] U.S. Cl. .................................... 514/255; 514/410; 548/421; 544/295
[58] Field of Search ........................ 548/421; 544/295; 514/410, 255

[56] References Cited

U.S. PATENT DOCUMENTS 3,892,756  7/1975  Nedelec et al. ........................ 546/72
4,064,139  12/1977 Anderson et al. .................. 548/425
4,374,838  2/1983  Anderson et al. .................. 514/289
4,399,141  8/1983  Anderson et al. .................. 514/294

FOREIGN PATENT DOCUMENTS 0002512  6/1979  European Pat. Off. .
0011206  5/1980  European Pat. Off. .
0230370  7/1987  European Pat. Off. .

OTHER PUBLICATIONS

Foster, et al., *Taking apart NMDA receptors*, Nature, 329, p. 395 (1987).
Kemp, et al., *Non-competitive antagonists of excitatory amino acid receptors*, Trends in Neurosciences, 10, p. 294 (1987).
Schwarcz, et al., *Excitatory Aminoacid Antagonists Provide a Therapeutic Approach to Neurological Disorders*, The Lancet, vol. II, p. 140 (1985).
Robinson, et al., A Novel Rearrangement Forming 4,5,6,11-*Tetrahydrobenzo*[6,7]*Cycloocta*[1,2-b]*thiophen*-6,11-*imines*, Tetrahedron Letters, 30, p. 5203 (1989).

Primary Examiner—Mukund J. Shah
Assistant Examiner—Matthew V. Grumbling
Attorney, Agent, or Firm—William T. Han

[57] ABSTRACT

Naphthothiophenimines of formula I

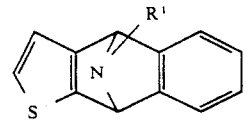

wherein $R^1$ is, inter alia, alkyl, cycloaklyl, alkenyl, phenalkyl or aminoalkyl.

Formula I compounds are useful in treating brain ischemia and resulting disorders.

18 Claims, No Drawings

NAPHTHOTHIOPHENIMINES FOR TREATING NEURONAL DISORDERS CAUSED BY ISCHEMIA

BACKGROUND OF THE INVENTION

This invention relates to novel naphtho[2,3-b]thiophen4,9-imines having specific non-competitive N-methyl-D-aspartate (NMDA) antagonist activity. For convenience the compounds of this invention will hereinafter be referred to as "naphthothiophenimines."

Recent findings have shown that the NMDA receptor plays a critical role in many complex neurophysiological and plastic events comprising central neural development and function. Evidence from animal studies has indicated that selective NMDA receptor antagonists can possess anticonvulsant, anxiolytic, anti-epileptic and muscle relaxant activity and can prevent neuronal degeneration caused by ischaemia, anoxia, hypoglycaemia and endogenous neurotoxins. More detailed discussion on this subject can be found in: Foster, et al., *Nature*, 329. p 395 (1987); Kemp, et al., *Trends in Neurosciences*, 10, p 294 (1987); and Schwarcz, et al., *The Lancet*, Vol. II p 140 (1985). Thus the novel compounds of this invention are intended for use in treating various neuronal disorders, particulary those induced by ischemia.

DESCRIPTION OF RELATED ART

A number of NMDA receptor antagonists have been described in the following patents and publications.

(a) U.S. Pat. No. 4,064,139 (issued on 12/20/77 to Anderson et al.) discloses, inter alia, compounds of Formula 1

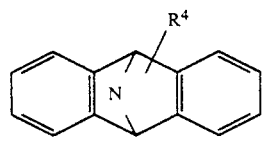

wherein $R^4$ is hydrogen, alkyl, aralkyl, alkenyl, dialkylaminoalkyl, cycloalkyl, or alkylcycloalkyl, as tranquilizers, anticonvulsants, muscle relaxants, and agents for treating extrapyramidal disorders.

(b) U.S. Pat. No. 3,892,756 (issued on 7/1/75 to Nedelec et al.) discloses, inter alia compounds of formula 2

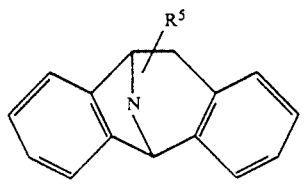

wherein $R^5$ is hydrogen, $C_{1-6}$alkyl, or lower alkenyl, as CNS stimulants possessing anticonvulsant activity.

(c) U.S. Pat. No. 4,399,141 (issued on 8/16/83 to Anderson el al.) relates to, inter alia, anticonvulsant compounds of formula 3

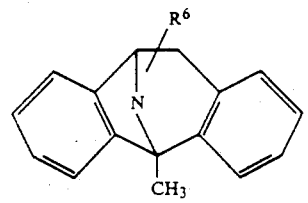

wherein $R^6$ is hydrogen, lower alkyl, lower alkenyl, phenyl-lower alkyl, lower cycloalkyl, lower (cycloalkyl-alkyl), or di(lower alkyl)amino-lower alkyl.

(d) U.S. Pat. No. 4,374,838 (issued 2/22/83 to Anderson et al.) discloses, inter alia, compounds of formula 4

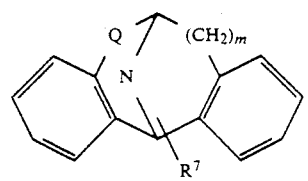

wherein
m is 0 or 1;
Q is —CH$_2$— when m is 1;
Q is —CH$_2$CH$_2$— or —CH=CH— when m is 0; and
$R^7$ is hydrogen, lower alkyl, lower alkenyl, phenyl-lower alkyl, lower cycloalkyl, and lower (cycloalkyl-alkyl), as anxiolytics, antidepressants, anticonvulsants, muscle relaxants, agents for treating extrapyramidal disorders, etc.

(e) European Patent Application No. 230,370 (published 7/29/87) discloses the use of the compounds described in the foregoing items (a), (c) and (d) as N-methyl-D-aspartate (NMDA) receptor antagonists which are useful in treating neurodegeneration of the hippocampus following ischemia induced by occlusion of the carotid arteries. A preferred species is MK-801 of the formula

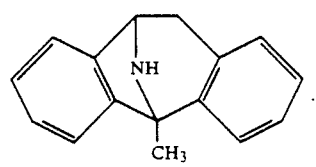

(f) European Patent Application No. 011,206 (published 5/28/80) discloses, inter alia, compounds of formula 5

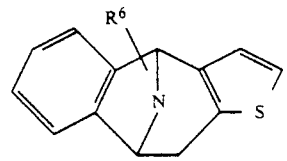

wherein $R^6$ is as defined previously in item (c), as antianxiety agents, muscle relaxants, and agents for treating extrapyramidal disorders.

(g) European Patent Application 002,512 (published 6/27/79) discloses, inter alia, compounds of formulas 6a and 6b

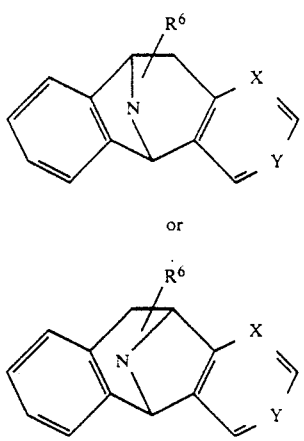

wherein X and Y are independently N or CH but cannot be the same, and $R^6$ is as defined previously in item (c).

(h) Robinson et al., in *Tetrahedron Letters*, 30, p. 5203 (1989), disclose NMDA receptor antagonists of formula 7

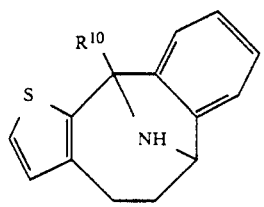

in which $R^{10}$ is hydrogen or methyl.

SUMMARY OF THE INVENTION

The present invention relates to new naphthothiophenimines of formula I

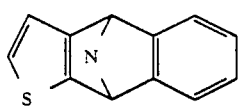

wherein $R^1$ is a straight or branched $C_{1-5}$ alkyl, $C_{3-5}$ alkenyl, benzyl or a radical selected from the group consisting of

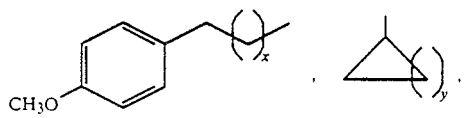

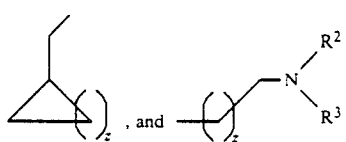

in which x is 0 to 2; y is 1, 3 or 4; z is 1 to 3; and $R^2$ and $R^3$ are independently $C_{1-3}$ alkyl, hydrogen, or $R^2$ and $R^3$ taken together constitute the radical

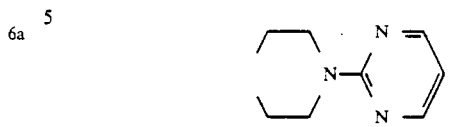

Pharmaceutically acceptable acid salts and/or solvates of the new naphthothiophenimines are also understood to be included as well as the base forms.

This invention also relates to pharmaceutical compositions comprising compounds of formula I and to methods of treatment of various neuronal disorders, particulary those resulting from ischemia of the brain, comprising administering such compounds and compositions.

DETAILED DESCRIPTION OF THE INVENTION

In its broadest aspect, the present invention relates to new naphthothiophenimines of the formula I and its pharmaceutically acceptable acid addition salts and/or solvates.

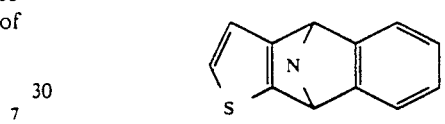

In formula I, $R^1$ is a straight or branched $C_{1-5}$ alkyl, $C_{3-5}$ alkenyl, benzyl or a radical selected from the group consisting of

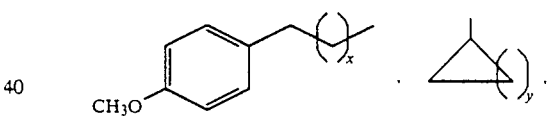

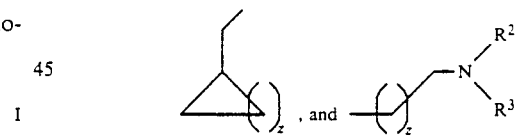

in which X is 0 to 2; y is 1, 3 or 4; z is 1 to 3; and $R^2$ and $R^3$ are independently $C_{1-3}$ alkyl, hydrogen, or $R^2$ and $R^3$ taken together constitute the radical

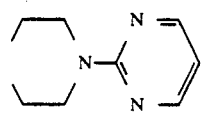

Compounds of formula I are useful as agents for treating neuronal disorders particularly those resulting from ischemia of the brain.

This application therefore relates to compounds of formula I, to pharmaceutical compositions comprising such compounds, and to methods of treating various neuronal disorders comprising administering such compounds and compositions.

It is to be understood that the present invention is considered to include the various stereoisomers, e.g., optical isomers including individual enantiomers, mixtures of enantiomers, diastereomers, and mixtures of diastereomers, which can arise as a consequence of structural asymmetry due to the presence of one or two asymmetric carbon atoms which may be incorporated in some compounds of the instant series. Separation of the individual isomers is accomplished by application of various methods which are well known to practitioners in the art.

The pharmaceutically acceptable acid addition salts of formula I compounds are those in which the anion does not affect the stability of the compounds and does not contribute significantly to the toxicity of the salt. They should be compatible with the customary pharmaceutical vehicles and adapted for oral or parenteral administration. The pharmaceutically acceptable acid addition salts include the salts of compounds of formula I with weak acids such acetic acid, benzoic acid, fumaric acid, mandelic acid, maleic acid, and the like. Preparation of these salts is carried out by conventional techniques involving reaction of compounds of formula I with the acid in a substantially equivalent amount. Additionally, the present invention also encompasses compounds of formula I existing in a solvate form such as a hydrate.

The mode of systemic administration, dosage, and dosage regimen must in each case be carefully adjusted by utilization of sound professional judgment and consideration of the age, weight and condition of the recipient. Generally, the daily dose will be from about 0.1 g to about 10 g, preferably 0.5 g to 5 g, when given orally. In some instances, a sufficient therapeutic effect can be obtained at lower doses while in others, larger doses will be required. As is apparent to one skilled in clinical pharmacology, the amount of a formula I compound comprising the daily dose may be given in a single or divided dose, taking into account those principles understood by the skilled practitioner and necessary for his practice of the art.

The term "systemic administration" as used herein refers to oral, sublingual, buccal, nasal, dermal, rectal, intramuscular, intravenous, and subcutaneous routes. Generally, it will be found that should a compound of the present invention be administered orally, a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective neuro-protective amount of a compound of formula I or a pharmaceutically acceptable acid addition salt thereof and a pharmaceutically acceptable carrier. Pharmaceutical compositions for effecting such treatment will contain a major or minor amount (e.g. from 95% to 0.5%) of at least one compound of the present invention in combination with pharmaceutical carrier, the carrier comprising one or more solid, semi-solid, or liquid diluent, filler and formulation adjutant which is non-toxic, inert and pharmaceutically acceptable. Such pharmaceutical compositions are preferably in dosage unit forms; i.e. physically discrete units having a pre-determined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the pre-determined dosage regimen, usually a whole, half, third, or less of the daily dosage administered once, twice, three or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents, (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of the active compound in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

Compounds of formula I of the present invention are generally prepared via a cycloadditon of benzyne and thienopyrroles of formula II.

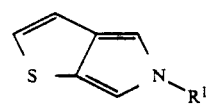

II in which $R^1$ is as defined hereinabove.

Thienopyrroles of formula II in turn can be made conveniently from the bromide of formula VIII by methods described by Sha et al., *J. Chem. Soc., Chem. Commun.*, p 1081 (1988).

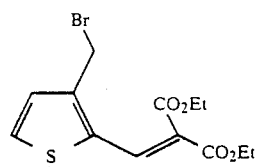

VIII

A preferred method of preparation of compounds of formula I in which $R^1$ is a radical of the formula

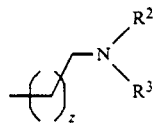

in which z, $R^2$ and $R^3$ are as defined previously, comprises the steps of:

a) forming a compound of formula III

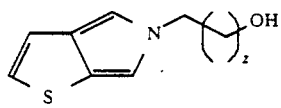

from an amino alcohol $H_2N(CH_2)_zOH$ by the method described by Sha et al. in *J. Chem. Soc., Chem. Commun.*, p. 1081(1988);

b) protecting the hydroxy group of the formula III compound with a conventional alcohol protecting group, $R^8$, preferably with t-butyldimethylsilyl to afford a compound of formula IV;

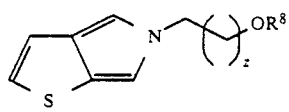

c) reacting a compound of formula IV with benzyne to afford a compound of formula V;

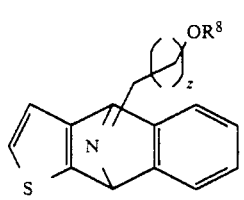

d) removing the protecting group, $R^8$, from a compound of formula V to afford an alcohol of the formula VI;

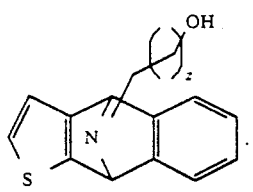

e) converting the alcohol moiety in a compound of formula VI into a leaving group to afford a compound of formula VII;

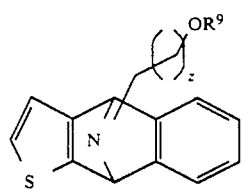

f) reacting an amine $HNR^2R^3$, in which $R^2$ and $R^3$ are as defined previously, with a compound of formula VI to afford a compound of formula I in which $R^1$ is a radical of the formula

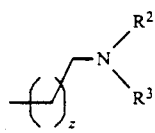

The aforementioned conversion of the hydroxy group in a compound of formula VI into a leaving group, $OR^9$, typically involves reacting a formula VI compound with methanesulfonyl chloride or p-toluenesulfonyl chloride in the presence of a base, preferably an organic amine base, such as triethylamine, pyridine, N,N-diethylpropylamine and the like, to afford a compound of formula VII in which $OR^9$ becomes mesylate or tosylate.

As used herein, conventional hydroxy protecting groups which can be employed in the present invention to block or protect the hydroxy function are well-known to those skilled in the art and, preferably, said groups can be removed, if desired, by methods which do not result in any appreciable destruction of the remaining portion of the molecule, for example by chemical or enzymatic hydrolysis. Examples of such readily removable hydroxy protecting groups include methoxymethyl, 2,2,2-trichloroethyoxymethyl, tetrahydropyranyl, tetrahydrofuranyl, t-butyl, p-methoxybenzyl, diphenylmethyl, trialkylsilyl, triphenylsilyl, and the like. A particularily advantageous hydroxy protecting group is t-butyldimethylsilyl which can be conveniently removed by fluoride ion. Other suitable protecting groups are disclosed in "Protecting Groups in Organic Synthesis", Theodora W. Greene (John Wiley & Sons, 1981), Chapter 2 for hydroxy, which is hereby incorporated by reference.

DESCRIPTION OF SPECIFIC EMBODIMENTS

The following methods, A to I, are general methods which can be applied to prepare compounds of the instant invention and intermediates thereof. Tables 1 and 2 contain representative compounds prepared, and the modes of their preparation and purification are shown. The methods disclosed may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), triplet (t), quartet (q), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers (cm$^{-1}$) having functional group identification value.

The abbreviations used in the present specification are conventional abbreviations well known to those skilled in the art, for example:

| | |
|---|---|
| iPrOH | isopropyl alcohol |
| CI | chemical ionization |
| ether | diethyl ether |
| THF | tetrahydrofuran |
| ppt | precipitate |
| eq. | equivalent(s) |

Synthesis of Thieno[2,3-c]pyrroles

Method A

5-Cyclopropylmethyl-5H-thieno[2,3-c]pyrrole (IIe):

A solution of cyclopropanemethylamine (3.07 g, 43.2 mmol) and bromide VIII (5.0 g, 14.4 mmol) in 75 mL of ethanol was stirred at room temperature for 1 h, then partitioned between ether and water. The organic phase was washed with brine, dried over magnesium sulfate, filtered, and concentrated in vacuo to give a dark oil. Purification by alumina column chromatography (hexanes) provided 2.07 g (81% yield) of an oil.

Method B 5-(2-t-Butyldimethylsilyloxyethyl)-5H-thieno[2,3-c]pyrrole (IVa):

A solution of t-butyldimethylsilyl chloride (710 mg, 4.71 mmol), 4-dimethylaminopyridine (18 mg, 0.145 mmo alcohol IIIa (605 mg, 3.62 mmol), prepared according to Method A, and triethylamine (733 mg, 7.24 mmol) in 40 mL of methylene chloride was stirred at room temperature for 24 h. Water (40 mL) was added to the reaction mixture and the methylene chloride removed in vacuo. The aqueous residue was partitioned between ether and water and the organic phase was washed with brine. The aqueous phases were further extracted with ether and the combined organic phases were dried over sodium sulfate, filtered, and concentrated in vacuo to give 1.3 g of a light brown liquid. Purification by alumina (23:1) column chromatography (ethyl acetate/hexanes, 1:99) provided 500 mg (49% yield) of a clear, colorless oil.

Method C

Alternate preparation of 5-Cyclopropylmethyl-5H-thieno[2,3-c]pyrrole (IIe):

A solution of cyclopropylmethylamine (8.20 g, 115 mmol), bromide VIII (20.0 g, 57.6 mmol), and potassium carbonate (15.9 g, 115 mmol) in 300 mL of ethanol was stirred at room temperature for 2 h. Water was added to the reaction mixture, the ethanol was removed in vacuo, and the remaining aqueous phase was extracted with ether. The combined organic phases were washed with water and brine, dried over magnesium sulfate, filtered, and concentrated in vacuo to give a black oil. Purification by alumina (20:1) column chromatography (EtOAc/hexanes, 1:49) provided 8.4 g (82%) of a light brown oil which was used immediately in the next reaction.

Data for Thieno[2,3-c]pyrroles (IIa):

5-Benzyl-5H-thieno[2,3-c]pyrrole (IIa):

$^1$H NMR (CDCl$_3$, 200 MHz): 7.25–7.33 (m 3H) 7.10–7.14 (m, 2H), 6.87–6.94 (m,3H), 6.78 (d, J=1.8 Hz, 1H), and 5.18 (s, 2H).

$^{13}$NMR (CDCl$_3$, 50 MHz): 137.7, 132.6, 128.8, 127.9, 127.1, 125.7, 124.1, 116.0, 110.0, 109.8, and 54.6.

IR (KBr): 3116, 3029, 2926, 1604, 1567, 1501, 1496, 1465, 1456, 1394, 1359, 1147, 749, and 709 cm$^{-1}$

MS (DCI, CH$_4$): 214.

Analysis for C$_{13}$H$_{11}$NS Calcd: C, 73.21; H, 5.20; N, 6.57. Found: C, 73.18; H, 5.23; N, 6.68.

5-Cyclyclopropyl-5H-thieno[2,3-c]pyrrole (IIb):

$^1$H NMR (CDCl$_3$, 200 MHz): 6.98 (d, J=2.0 Hz, 1H), 6.94 (d, J=5.4 Hz, 1H), 6.84–6.88 (m, 2H), 3.49–3.60 (m, 1H), and 0.89–1.08 (m, 4H).

$^{13}$C NMR (CDCl$_3$, 50 MHz): 132.0, 125.7, 123.4, 115.8, 110.0, 109.9, 31.3, and 6.6.

IR (Kbr): 3126, 3081, 3011, 2922, 1732, 1563, 1503, 1464, 1451, 1403, 1351, 1164, 1071, 1027, 749, and 611 cm$^{-1}$.

MS (CI, CH$_4$): 164.

5-Cyclohexyl-5H-thieno[2,3-c]pyrrole (IIc):

$^1$H NMR (CDCl$_3$, 200 MHz): 6.97 (d, J=1.8 Hz, 1H), 6.91 (s, 2H), 6.86 (d, J=1.8 HZ, 1H), 3.94 (t of t, J=13.2 and 3.3 Hz), 2.09–2.23 (m, 2H), 1.60–2.00 (m, 5H), and 1.15–1.58 (m, 3H).

$^{13}$C NMR (CDCl$_3$, 50 MHz): 131.7, 125.1, 123.0, 115.9 107.3, 107.2, 60.2, 35.0, 25.6, and 25.5.

IR KBr: 3132, 2934, 2857, 1730, 1561, 1500, 1460, 1449, 1384, 1149, 1140, and 751 cm$^{-1}$.

MS (CI, CH$_4$): 206.

Analysis for C$_{12}$H$_{15}$NS Calcd: C, 70.20; H, 7.36; N, 6.82. Found: C, 70.05; H, 7.44; N, 6.48.

5-Cyclopropylmethyl-5H-thieno[2,3-c]pyrrole (e,uns/IIe):

$^1$H NMR (CDCl$_3$, 200 MHz): 6.95 (d, J=2.0 Hz, 1H), 6.90 (s, 2H), 6.83 (d, J=1.8 Hz, 1H), 3.88 (s, 1H), 3.84 (s, 1H), 1.15–1.30 (m, 1H), 0.58–0.67 (m, 2H), and 0.30–0.38 (m, 2H).

$^{13}$C NMR (CDCl$_3$, 50MHz): 132.2, 125.2, 123.6, 115.9, 109.2, 109.0, 55.5, 12.3, and 4.1.

IR (thin film): 3126, 3078, 3003, 2925, 1732, 1686, 1567, 1504, 1466, 1390, 1327, 1283, 1144, 1022, and 743 cm$^{-1}$.

MS CI, CH$_4$): 178.

5-(2-Hydroxyethyl 5H-thieno[2,3-c]pyrrole (IIIa):

$^1$H NMR (CDCl$_3$, 300 MHz): (spectrum indicated presence of ethanol; only product peaks reported) 6.93 (d, J=5.4 Hz, 1H), 6.90 (d, J=1.9 Hz, 1H), 6.88 (d, J=5.4 Hz, 1H), 6.78 (d, J=1.9 Hz, 1H), 4.08 (t, J=5.1 Hz, 2H), 3.81 (t, J=5.1 Hz, 2H), and 1.95 (br s, 1H). $^{13}$C NMR (CDCl$_3$, 75 MHz): 133.1, 126.2, 124.7, 116.2, 110.1, 109.8, 63.3, and 53.5.

MS (CI, CH$_4$): 168.

5-(2-t-Butyldimethylsilyloxyethyl)-5H-thieno[2,3-c]pyrrole (Iva):

$^1$H NMR (CDCl$_3$ 300 MHz): 6.88–6.92 (m, 3H), 6.80 (d, J=1.7 Hz, 1H), 4.11 (t, J=5.6 Hz, 2H), 3.89 (t, J=5.6 Hz, 2H), 0.87 (s, 9H), and −0.04 (s, 6H). $^{13}$C NMR (CDCl$_3$, 75 MHz): 132.1, 125.1, 123.5, 115.7, 109.7, 109.5, 63.6, 53.2, 25.7, 25.5, and 18.1.

IR (KBr): 3126, 2955, 2929, 2857, 1569, 1503, 1472, 1395, 1361, 1284, 1258, 1216, 1149, 1114, 1072 1007, 929, 838, 779, and 742 cm$^{-1}$.

MS (CI, CH$_4$) 282.

5-p-Methoxyphenethyl-5H-thieno[2,3-c]pyrrole (IIk):

$^1$H NMR (d$_6$-DMSO, 300 MHz): 7.07–7.13 (m, 2H), 6.98–7.05 (m, 3H), 6.82–6.92 (m, 3H), 4.28 (t, J=7.4 Hz, 2H), 3.72 (s, 3H), and 3.03 (t, J=7.4 Hz, 2H).

Synthesis of Naphthothiophenimines

Method D

10-Cyclopropylmethyl-4,9-dihydronaphtho[2,3-b]thiophen-4,9-imine (Ie):

n-Butyllithium solution (9.0 mL, 2.5M in hexanes, 22.4 mmol) was added via addition funnel over 2 h to a solution of 5-cyclopropylmethyl-5H-thieno[2,3-c]pyrrole (IIe) (3.62 g, 20.4 mmol) and 1,2-dibromobenzene (5.28 g, 22.4 mmol) in 200 mL of THF at −78° C. The resulting brown solution was stirred at −78° C. for 30 min before the cooling bath was removed. After stirring at room temperature for 30 min, water was added to the reaction mixture, the THF was removed in vacuo and ether was added. The organic phase was isolated and washed with brine. The aqueous phases were extracted with ether and the combined organic phases were dried over magnesium sulfate, filtered and concentrated in vacuo. Purification of the residue by silica gel column chromatography (EtOAc/hexanes gradient) and recrystallization from EtOAc/hexanes (1:1) provided 1.0 g (19%) of an off-white solid: mp 129°-130° C.

Method E 10-(2-Hydroxyethyl)-4,9-dihydronaphtho[2,3-b]thiophen-4,9-imine (VIa):

Tetrabutylammonium fluoride solution (3.70 mL, 1.0M in THF, 3.70 mmol) was added dropwise over 10 min to a solution of silyl ether Va (1.10 g, 3.08 mmol) in 30 mL of THF at 0° C. The resulting mixture was allowed to warm slowly to room temperature with stirring overnight. The crude reaction mixture was partitioned between ether and water and the organic phase was washed with brine. The aqueous phases were then further extracted with ether and the combined organic phases were dried over magnesium sulfate, filtered, and concentrated in vacuo to give 1.21 g of a brown solid. Purification by silica gel (21:1) column chromatography (EtOAc) and recrystallization from EtOAc provided 247 mg (33%) of off-white flakes: mp 157°-158° C.

Method F 10-(2-Methanesulfonylethyl)-4,9-dihydronaphtho[2,3-b]thiophen-4,9-imine (VIIa):

Methanesulfonyl chloride (672 mg, 5.87 mmol) was added dropwise over 5 min to a solution of alcohol VIa (1.30 g, 5.34 mmol) and triethylamine (810 mg, 8.01 mmol) in 27 mL of methylene chloride at 0° C. The resulting mixture was stirred for 2 h at 0° C. then washed with cold (0° C.) water, cold saturated aqueous bicarbonate solution, and cold brine. The aqueous phases were extracted in sequence with methylene chloride and the combined organic phases were dried over magnesium sulfate, filtered, and concentrated in vacuo to provide 1.7 g of a light brown solid which was used without purification.

Method G

10-[2-[4-(2-pyrimidinyl)-1-piperazinyl]ethyl]-4,9-dihydronaphtho[2,3-b]thiophen-4,9-imine (Ih):

A mixture of mesylate VIIa (1.69 g, 5.26 mmol), triethylamine (1.06 g, 10.5 mmol), and (2-pyrimidinyl)-1-piperazine (950 mg, 5.79 mmol) in 50 mL of acetonitrile was heated to reflux for 29 h. The reaction mixture was partitioned between ether and water and the organic phase was washed with brine. The aqueous phases were extracted with ether and the combined organic phases were dried over magnesium sulfate, filtered, and concentrated in vacuo to provide 1.98 g of a yellow solid. Purification by silica gel (25:1) column chromatography (ethanol/methylene chloride, 2-5% gradient) and recrystallization from acetonitrile provided 1.09 g (53% yield) of white flakes.

Method H

10-[2-(N,N-dimethylamino)ethyl]-4,9-dihydronaphtho[2,3-b]-thiophen-4,9-imine (Im):

A solution of mesylate VIIa (1.67 g, 5.20 mmol) and dimethylamine (excess) in 60 mL of acetonitrile was heated in a bomb at 70° C. for 4 h and then partitioned between water and ether. The organic phase was washed with brine and the aqueous phases were extracted with ether. The combined organic phases were dried over magnesium sulfate, filtered, and concentrated in vacuo to provide 1.43 g of a light brown oil. Purification by silica gel column chromatography (MeOH/CH$_2$Cl$_2$/NH$_4$OH gradient) provided 1.20 g (85%) of a pink solid.

Data for Naohthothioohenimines

10-Benzyl-4,9-dihydronaphtho[2,3-b]thiophen-4,9-imine (Ia):

mp: 118°-119° C.

$^1$H NMR (CDCl$_3$, 200 MHz): 7.15-7.35 (m, 7H), 6.85-6.95 (m, 4H), 5.00 (s, 1H), 4.96 (s, 1H), and 3.69 (brs, 2H)

$^{13}$C NMR (CDCl$_3$, 50 MHz): (non-aromatic signals only) 69.5, 69.3, and 54.4.

IR (KBr): 3077, 3063, 3025, 2999, 2922, 2893, 2850, 2815, 1493, 1452, 1363, 1264, 1239, 1181, 1133, 1072, 785, 760, 740, 712, 701, 688, and 667 cm$^{-1}$.

MS (DCI, CH$_4$): 290.

Analysis for C$_{19}$H$_{15}$NS Calcd: C, 78.85; H, 5.22; N, 4.84. Found: C, 78.68; H, 5.39; N, 4.68.

Material obtained from a separate run was characterized by variable temperature NMR: $^1$H NMR (d$_6$-DMSO, 360 MHz, 21° C.) 7.14-7.33 (m, 8H), 7.03 (br, 1H), 6.90 (br, 2H), 5.11 (s, 1H), 4.98 (s, 1H), 3.32 and 3.30 (two s, combined integration of 2H).

$^1$H NMR (d$_6$-DMSO, 360 MHz, 55° C.): 7.20-7.33 (m, 7H), 7.11 (d, J=4.5 Hz, 1H), 7.01 (d, J=4.5 HZ, 1H), 6.87-6.95 (m, 2H), 5.10 (s, 1H), 4.98 (s, 1H), and 3.10 (s, 2H).

10-Cyclopropyl-4,9-dihydronaphtho[2,3-b]thiophen-4,9-imine (Ib):

mp: 140°−142° C·

$^1$H NMR (CDCl$_3$, 200 MHz): 7.15-7.35 (m, 2H), 6.85-6.95 (m, 4H), 5.15 (s, 1H), 5.09 (s, 1H), 2.02 (br s, 1H), 0.57-0.64 (m, 2H), 0.38-0.46 (m,2H).

$^{13}$C NMR (CDCl$_3$, 50 MHz): (non-aromatic signals only) 70.9, 70.6, 30.8, and 6.1.

IR (KBr): 3075, 3003, 2955, 1734, 1451, 1364, 1269, 1239, 1206, 1188, 115.3, 1133, 1007, 807, 763, 736, 713, and 671 cm$^{-1}$.

MS (CI, CH$_4$): 240 (100%), 194 , and 184.

Analysis for C$_{15}$H$_{13}$NS Calcd: C, 75.28; H, 5.47; N, 5.85 Found: C, 75.46; H, 5.59; N, 5.78.

10-Methyl-4,9-dihydronaphtho[2,3-b]thiophen-4,9-imine (Id):

mp: 147°-147.5° C $^1$H NMR (CDCl$_3$, 300 MHz, 22° C.): 7.18-7.27 (m, 2H), 6.84-6.96 (m, 4H), 4.97 (s, 1H), 4.90 (s, 1H), 2.40 and 2.27 (br, 3H).

$^1$H NMR (CDCl$_3$, 300 MHz, 47° C.): 7.19-7.24 (m, 2H), 6.89-6.93 (m, 4H), 4.94 (s, 1H), 4.88 (s, 1H), and 2.36 (s, 3H).

$^1$H NMR (d$_6$-DMS0, 300 MHz): 7.23 (br, 2H), 7.12 (br, 1H), 7.00 (d, J=4.5 Hz, 1H), 6.88 (br, 2H), 5.08 (s, 1H), 4.94 (s, 1H), 2.25 and 2.12 (br, 3H).

$^{13}$C NMR (CDCl$_3$, 75 MHz): (non-aromatic signals only) 71.9, 71.6 and 37.1.

IR (KBr): 3087, 3072, 3005, 2972, 2948, 2853, 2771, 1733, 1453, 1438, 1273, 1240, 1217, 1200, 1138, 1096, 737, 715, and 670 cm$^{-1}$ MS (CI, CH$_4$): 214.

Analysis for C₁₃H₁₁NS Calcd: C, 73.20; H, 5.20; N, 6.57. Found: C, 72.85; H, 5.42; N, 6.64.

In a separate run, the fumaric acid salt was prepared from 4.12 g (19.3 mmol) of the free imine in CHCN/i-PrOH and 2.25 g (19.3 mmol) of fumaric acid in iPrOH. Recrystallization of the ppt from iPrOH provided 2.65 g (42%) of the salt as a tan solid:

mp 105°–107° C. (dec).

$^1$H NMR (d₆-DMSO, 300 MHz): 7.25 (br, 2H), 7.14 (br, 1H), 7.03 (d, J=4.5 Hz, 1H), 6.91 (br, 2H), 6.61 (s, 2H), 5.18 (br s, 1H), 5.05 (br s, 1H) and 2.27 (br, 3H).

$^{13}$C NMR (d₆-DMSO 90 MHz) (non-aromatic signals only) 166.2, 134.1, 70.8, 70.5 and 36.4.

IR (KBr): 3432 (br), 1699, and 1682 cm⁻¹.

MS (CI, CH₄): 214 and 117 (100%).

Analysis for C₁₃H₁₁NS/C₄H₄O₄ Calcd: C, 61.99; H, 4.59; N, 4.25. Found: C, 62.31; H, 4.66; N, 4.43.

10-Cyclopropylmethyl-4,9-dihydronaphtho[2,3-b]thiophen-4,9-imine (Ie):

mp: 129°–130° C.

$^1$H NMR (d₆-DMSO, 300 MHz, 24° C.): 7.22–7.26 (m, 2H), 7.07–7.12 (m, 1H), 6.99 (d, J=4.5 Hz, 1H), 6.84–6.91 (m, 2H), 5.28 (s, 1H), 5.14 (s, 1H), 2.27 (br, 2H), 0.80–0.93 (m, 1H), 0.40–0.48 (m, 2H), and −0.10–0.03 (m, 2H).

$^1$H NMR (d₆-DMSO, 300 MHz, 52° C.): 7.21–7.26 (m, 2H), 7.06 (d, J=4.6 Hz, 1H), 6.98 (d, J=4.6 Hz, 1H), 6.85–6.91 (m, 4H), 5.25 (s, 1H), 5.13 (s, 1H), 2.25 (d, J=6.6 Hz, 2H), 0.81–0.94 (m, 1H), 0.40–0.50 (m, 2H), and −0.03–0.01 (m, 2H).

$^{13}$C NMR (CDCl₃, 50 MHz): (non-aromatic signals only) 69.6, 69.4, 54.6, 9.8, and 3.5.

IR (KBr): 3076, 3048, 3000, 2924, 3892, 2831, 1457, 1451, 1423, 1393, 1329, 1260, 1135, 1100, 1083, 1053, 1020, 897, and 748 cm⁻¹.

MS (CI, CH₄): 254 (100%), 208, 198, 185, and 173.

Analysis for C₁₆H₁₅NS Calcd: C, 75.85; H, 5.97; N, 5.53. Found: C, 75.75; H, 6.00; N, 5.52.

In a separate run, the fumaric acid salt was prepared from 939 mg (3.71 mmol) of the free imine in acetonitrile at room temperature and 431 mg (3.71 mmol) of fumaric acid in warm ethanol. The ppt was collected by filtration and dried in vaciuo at room temperature to provide 1.15 g (84%) of a white solid:

mp: 123° C. (with sublimation).

$^1$H NMR (d₆-DMSO, 300 MHz): 7.21–7.28 (m, 2H), 7.10 (d, J=4.5 Hz, 1H), 7.0 (d, J=4.6 Hz, 1H), 6.87–6.90 (m, 2H), 6.60 (s, 2H), 5.33 (s, 1H), 5.19 (s, 1H), 2.27 (br, 2H), 0.80–0.95 (m, 1H), 0.42–0.45 (m, 2H), −0.06–−0.02 (m, 2H).

MS (CI, CH₄): 254 and 117.

IR (KBr): 3422 (br) and 1680 cm⁻¹.

Analysis for C₂₀H₁₉NSO₄ Calcd: C, 65.03; H, 5.19; N, 3.80. Found: C, 64.65; H, 5.17; N, 3.68.

10-Cyclohexyl-4,9-dihydronaphtho[2,3-]thiophen-4,9-imine (Ic):

mp: 147°–152° C.

$^1$H NMR (CDCl₃, 200 MHz): 7.17–7.25 (m, 2H), 6.85–6.95 4H), 5.30 (s, 1H), 5.24 (s, 1H) 2.25 (br s, 1H), 1.50–1.90 (m, 5H), 1.00–1.40 (m, 5H).

$^{13}$C NMR (CDCl₃, 50 MHz): (non-aromatic signals only) 67.1 66.8, 55.2, 31.3, 25,8, and 24.8

IR (KBr): 3096, 3067, 3013, 2932, 2903, 2855, 1451, 1447, 1102, 794, 751, 715, 691, and 669 cm⁻¹.

MS (CI, CH₄): 282.

Analysis for C₁₈H₁₉NS Calcd: C, 76.82; H, 6.80; N, 4.98. Found: C, 76.72; H, 6.88; N, 4.89.

10-Allyl-4,9-dihydronaphtho[2,3-b]thiophen-4,9-imine (Ij):

$^1$H NMR (d₆-DMSO, 300 mHz): 7.24–7.28 (m, 2H), 7.10–7.15 (m, 1H), 7.02 (d, J=4.7 Hz, 1H), 6.85–6.94 (m, 2H), 5.80–5.94 (m, 1H), 5.19 (s, 1H), 5.03–5.12 (m, 3H), and 3.04 (br, 2H).

MS (CI, CH₄): 240, 198, 194, 184, and 173.

Conversion to the fumaric acid salt (MeOH/acetonitrile) provided 0.8 g of a white solid:

mp 190° C. (dec).

$^1$H NMR (d₆-DMSO, 300 MHz): 7.25–7.29 (m, 2H), 7.10–7.15 (m, 1H), 7.03 (d, J=4.5 Hz, 1H), 6.90–6.95 (m, 2H), 6.64 (s, 2H), 5.81 5.94 (m, 1H), 5.21 (s, 1H), 5.04–5.13 (m, 3H), and 3.05 (br, 2H).

IR (KBr): 3031, 2826, 2463, 1702, 1639, 1543, 1456, 1386, 1281, 1250, 1175, 983, 941, 798, 770, 718, 685, 672, 646, and 570 cm⁻¹.

MS (CI, CH₄): 240, 117.

Analysis for C₁₅H₁₃NS/C₄H₄O₄/0.03 H₂O Calcd: C, 64.12; H, 4.84; N, 3.92; H₂O, 0.15 Found: C, 63,98; H, 4.68; N, 3.94; H₂O, 0.15.

10-Isopropyl-4,9-dihydronaphtho[2,3-b]thiophen-4,9-imine (Ii):

$^1$H NMR (d₆-DMSO, 300 MHz): 7.15–7.25 (m, 2H), 7.04–7.10 (m, 1H), 6.95 (d, 1H, 6.80–6.89 (m, 2H), 5.32 (s, 1H), 5.18 (s, 1H), 2.40 (br, 1H), and 0.90–1.00 (m, 6H).

Conversion to the fumaric acid salt (MeOH/acetonitrile) provided 1.50 g of a white solid:

mp: 180° C. (dec).

$^1$H NMR (d₆-DMSO, 300 MHz): 7.21–7.30 (m, 2H), 7.12 (d, J=4.6 Hz, 1H), 7.01 (d, J=4.6 Hz, 1H), 6.90–6.92 (m, 2H), 6.63 (s, 2H), 5.41 (s, 1H), 5.28 (s, 1H), 2.45 (br, tertiary proton of isopropyl group not easily detectable), and 0.97–1.01 (m, 6H).

IR (KBr): 3434, 1706, 1640. 1601, 1585, 1455, 1383, 1259, 1180, 1127, 983, 717, 681, 648, 625, 595, and 590 cm⁻¹.

MS (CI, CH₄): 242 and 117.

Analysis for C₁₅H₁₅NS/C₄H₄O₄/0.25 H₂O Calcd: C, 63.06; H, 5.44; N, 3.88; H₂O, 1.24. Found: C, 62.99; H, 5.30; N, 3.90; H₂O, 1.15.

10-Methoxyphenethyl)-4,9-dihydronaphtho[2,3-b]thiophen-4,9-imine (Ik):

mp: 118°–120° C.

$^1$H NMR (d₆-DMSO, 300 MHz): 7.18–7.25 (m, 2H), 7.08–7.09 (m, 1H), 7.03 (d, J=8.5 Hz, 2H), 6.98 (d, J=4.6 Hz, 1H), 6.85–6.88 (m, 2H), 6.77 (d, J=8.6 Hz, 2H), 5.23 (s, 1H), 5.09 (s, 1H), 3.66 (s, 3H), and 2.40–2.70 (m, 4H).

IR (KBr): 1610, 1513, 1462, 1452, 1300, 1242, 1180, 1089, 1039, 1030, 737, 713, and 671 cm⁻¹.

MS (CI, CH₄): 334.

Analysis for C₂₁H₁₉NOS/0.1 H₂O Calcd: C, 75.24; H, 5.78; N, 4.18; H₂O, 0.54. Found: C, 75.27; H, 6.04; N, 4.10; H₂O, 0.50.

10-Cyclobutylmethyl-4,9-dihydronaphtho[2,3-b]thiophen-4,9-imine (In):

$^1$H NMR (d₆-DMSO, 300 MHz): 7.18–7.24 (m, 2H), 7.05–7.10 (m, 1H), 6.97 (d, J=4.5 Hz, 1H), 6.85–6.87 (m, 2H), 5.12 1 (s, 1H), 4.98 (s, 1H), 2.30–2.45 (m, 3H), 1.90–2.05 (m, 2H), 1.67–1.88 (m, 2H), and 1.45–1.60 (m, 2H).

IR KBr): 2976, 2958, 2945, 2922, 2851, 1453, 1262, 1099, 1082, 746, 716, 674, and 656 cm⁻¹.

MS (CI, CH₄): 268 (100%), 222, 212, 200, 198, 185, and 173.

Conversion to the fumaric acid salt (acetonitrile/MeOH) provided 0.90 g of a white solid:
mp: 180° C. (dec).

$^1$H NMR (d$_6$-DMSO, 300 MHz): 7.18–7.25 (m, 2H), 7.09–7.10 (m, 1H), 6.98 (d, J=4.6 Hz, 1H), 6.86–6.89 (m, 2H), 6.61 (s, 2H), 5.15 (s, 1H), 5.01 (s, 1H), 2.35–2.45 (m, 3H), 1.92–2.05 (m, 2H), 1.67–1.88 (m, 2H), and 1.45–1.60 (m, 2H).

IR (KBr): 2968, 2521, 2473, 1699, 1638, 1549, 1459, 1452, 1390, 1302, 1277, 1250, 1208, 1173, 1144, 1102, 980, and 643 cm$^{-1}$.

MS (CI, CH$_4$): 450, 268, 117 (100%).

Analysis for C$_{17}$H$_{17}$NS/C$_4$H$_4$O$_4$/0.15 H$_2$O Calcd: C, 65.32; H, 5.57; N, 3.63; H$_2$O, 0.70. Found: C, 65.28; H, 5.49; N, 3.78; H$_2$O, 0.74.

10-[2-(t-Butyldimethylsilyloxy)ethyl]-4,9-dihydronaphtho[2,3-b]thiophen-4,9-imine (Va):

$^1$H NMR (CDCl$_3$, 300 MHz): 7.17–7.21 (m, 2H), 6.87–6.91 (m, 4H), 5.16 (s, 1H), 5.08 (s, 1H), 3.80 (t, J=6.0 Hz, 2H), 2.60 (br, signal does not integrate accurately), 0.87 (s, 9H), and 0.00 (s, 6H). 10-(2-Hydroxyethyl)-4,9-dihydronaphtho[2,3-b]thiophen-4,9-imine (VIa):

$^1$H NMR (d$_6$-DMSO, 300 MHz): 7.20–7.27 (m, 2H), 7.07–7.13 (m, 1H), 6.99 (d, J=4.6 Hz, 1H), 6.84–6.92 (m, 2H), 5.25 (s, 1H), 5.12 (s, 1H), 4.46–4.53 (m, 1H), 3.46–3.55 (m, 2H), and 2.47 (br, 2H).

IR (KBr): 3193 (br), 2942, 2861, 1455, 1264, 1065, 1054, 824, 750, 709, 671, and 663 cm$^{-1}$.

MS (DCI, CH$_4$): 244, 226, and 199.

Analysis for C$_{14}$H$_{13}$NOS Calcd: C, 69.11; H, 5.38; N, 5.76. Found: C, 68.89; H, 5.34; N, 5.68.

10-[2-(Methanesulfonyl)ethyl]-4,9-dihydronaphtho[2,3-b]thiophen-4,9-imine (VIIa):

$^1$H NMR (CDCl$_3$, 300 MHz): 7.22–7.25 (m, 2H), 6.92–6.94 (m, 4H), 5.16 (s, 1H), 5.09 (s, 1H), 4.39 (t, J=5.5 Hz, 2H), 2.98 (s, 3H), and 2.83 (br 2H).

$^{13}$C NMR (CDCl$_3$, 75 MHz): (non-aromatic signals only) 70.5, 70.2, 69.3, 49.2, and 37.7.

IR, (KBr): 1457, 1347, 1331, 1190, 1174, 1102, 981, 971, 940, 919, 907, 814, 792, 737, 716, 672, and 530 cm$^{-1}$.

MS (CI, CH$_4$): Consistent M+H observed at 322.

10-[2-[4-(2-Pyrimidinyl)-1-piperazinyl]ethyl]-4,9-dihydronaphtho[2,3-b]thiophen-4,9-imine (Ih):

$^1$H NMR (CDCl$_3$, 300 MHz): 8.28 (d, J=4.7 Hz, 2H), 7.17–7.24 (m, 2H), 6.89–6.93 (m, 4H), 6.45 (t, J=4.7 Hz, 1H), 5.24 (s, 1H), 5.14 (s, 1H), 3.78–3.82 (m, 4H), 2.50–2.80 (m, 4H), and 2.42–2.45 (m, 4H).

IR (KBr): 2839, 1585, 1547, 1485, 1469, 1460, 1450, 1361, 1308, 1252, 986, 800, 789, 741, and 661 cm$^{-1}$.

MS (CI, CH$_4$) 390, 205, 191 (100%), and 177.

Conversion to the fumaric acid salt (EtOH/acetonitrile) provided 1.24 g of an off-white solid:
mp: 139°–143° C. (dec).

$^1$H NMR (d$_6$-DMSO, 300 MHz): 8.33 (d, J=4.7 Hz, 2H), 7.20–7.30 (m, 2H), 7.08–7.15 (m, 1H), 7.01 (d, J=4.6 Hz, 1H), 6.88–6.90 (m, 2H), 6.59–6.62 (m, 3H), 5.33 (s, 1H), 5.20 (s, 1H), 3.70–3.73 (m, 4H), and 2.43–2.60 (m, 8H).

$^{13}$C NMR (d$_6$-DMSO, 75 MHz): (non-aromatic signals only) 69.5, 69.2, 56.6, 52.6, 46.1, and 43.1.

IR (KBr): 3441 br), 1692, 1678, 1654, 1588, 1550, 1479, 1455, 1370, 1307, 1280, 1261, 1171, and 980 cm$^{-1}$.

MS (CI, CH$_4$): 390 (100%), 191, 177, and 117.

Analysis for C$_{22}$H$_{23}$N$_5$S/C$_4$H$_4$O$_4$/0.1 H$_2$O Calcd: C, 61.55; H, 5.41; N, 13.81; H$_2$O, 0.36. Found: C, 61.30; H, 5.29; N, 13.58; H$_2$O, 0.36.

10-[2-(N,N-dimethylamino)ethyl]-4,9-dihydronaphtho[2,3-thiophen-4,9-imine (Im):

$^1$H NMR (CDCl$_3$, 300 MHz : 7.18–7.25 (m, 2H), 6.89–6.93 (m, 4H), 5.16 (s, 1H), 5.08 (s, 1H), 2.45–2.75 (m, 4H) and 2.17 (s, 6H).

IR (KBr): 2969, 2941, 2850, 2823, 2791, 2773, 1451, 1354, 1278, 1100, 1007, 766, 737, 707, 686, and 665 cm$^{-1}$.

MS (CI, CH$_4$): 271, 226, 212, and 184.

Conversion to the fumaric acid salt (acetonitrile/MeOH) provided 937 mg of a white solid:
mp: 142°–145° C. (dec).

$^1$H NMR (d$_6$-DMSO, 300 MHz): 7.20–7.27 (m, 2H), 7.05–7.15 (m, 1H), 6.99 (d, J=4.6 Hz, 1H), 6.87–6.89 (m, 2H), 6.50 (s, 2H), 5.30 (s, 1H), 5.17 (s, 1H), 2.75–2.79 (m, 2H), 2.50–2.70 (br, 2H), and 2.40 (s, 6H).

IR (KBr): 3432 (br), 2100–3100 (br), 1700, 1682, and 1624 cm$^{-1}$.

MS (CI, CH$_4$): 271, 117 (100%).

Analysis for C$_{16}$H$_{18}$N$_2$S/C$_4$H$_4$O$_4$ Calcd: C, 62.16; H, 5.74; N, 7.25. Found: C, 62.32; H, 5.68; N, 7.32.

10-[2-(N-methylamino)ethyl]-4,9-dihydronaphtho[2,3-thiophen-4,9-imine (Ir):

1H NMR (d$_6$-DMSO, 300 MHz): 7.20–7.24 (m, 2H), 7.08–7.09 (m, 1H), 6.98 (d, J=4.8 Hz, 1H), 6.84–6.90 (m, 2H), 5.22 (s, 1H), 5.09 (s, 1H), 2.30–2.92 (m, 4H), and 2.22 (s, 3H).

$^{13}$C NMR (d$_6$-DMSO, 75 MHz): (non-aromatic signals only) 69.3, 69.0, 50.3, 48.8, and 36.2.

IR (KBr): 3432 (br), 3278, 3042, 3008, 2958, 2928, 2902, 2850, 2788, 1484, 1450, 1262, 1200, 1122, 1100, 830, 778, 742, 712, 682, 662, and 604 cm$^{-1}$.

MS (CI, CH$_4$): 257 (100%), 226, 212, 200, 184, 173, and 85.

Conversion to the fumaric acid salt (acetonitrile/MeOH) provided 1.3 g of a white solid: mp: 150°–156° C. (dec).

$^1$H NMR (d$_6$-DMSO, 300 MHz): 7.20–7.30 (m, 2H), 7.08–7.19 (m, 1H), 7.01 (d, J=4.6 Hz, 1H), 6.89–6.91 (m, 2H), 6.41 (s, 2H), 5.31 (s, 1H), 5.18 (s, 1H), 2.85–2.95 (m, 2H), 2.50–2.70 (m, 2H), and 2.45 (s, 3H).

IR (KBr): 3438 (br), 2998, 2852, 2766, 2516, 1734, 1644, 1580, 1448, 1362, 1312, 1188, 984, 782 736, 714, 668, and 644 cm$^{-1}$.

MS (CI, isobutane): 257, 173 (100%), and 117.

Analysis for C$_{15}$H$_{16}$N$_2$S/C$_4$H$_4$O$_4$ Calcd: C, 61.27; H, 5.41; N, 7.52 Found: C, 61.20; H, 5.39; N, 7.57.

10-[2-(N,N-diethylamino)ethyl]-4,9-dihydronaphtho[2,3-b]thiophen-4,9-imine (Io):

1H NMR (d$_6$-DMSO, 300 MHz): 7.18–7.25 (m, 2H), 7.05–7.10 (m, 1H), 6.98 (d, J=4.6 Hz, 1H), 6.85–6.88 (m, 2H), 5.26 (s, 1H), 5.12 (s, 1H), 2.45–2.55 (m, 4H), 2.36 (q, J=7.1 Hz, 4H), and 0.89 (t, J=7.1 Hz, 6H).

$^{13}$C NMR (d$_6$-DMSO, 75 MHz): (non-aromatic signals only) 69.4, 69.2, 51.7, 46.7, and 11.8.

IR (KBr): 2964, 2924, 2798, 1450, 1380, 1348, 1290, 1094, 1072, 1028, and 736 cm$^{-1}$.

MS (CI, CH$_4$): 299, 100 (100%), and 86.

Conversion to the fumaric acid salt (acetonitrile/MeOH) provided 860 mg of a white solid: 148°–150° C.

1H NMR (d$_6$-DMSO, 300 MHz): 7.18–7.25 (m, 2H), 7.05–7.15 (m, 1H), 6.99 (d, J=4.6 Hz, 1H), 6.50 (s, 2H), 5.31 (s, 1H), 5.17 (s, 1H), 2.81 (t, J=6.7 Hz, 2H), 2.70 (q, J=7.2 Hz, 4H), 2.56 (br s, 2H), and 1.00 (t, J=7.2 Hz, 6H).

IR (KBr): 3432 (br), 3024, 2984, 2846, 1678, and 1624 cm$^{-1}$.

MS (CI, CH$_4$): 299, 117 (100%).

Analysis for $C_{18}H_{22}N_2S/C_4H_4O_4$ Calcd: C, 63.75; H, 6.32; N, 6.76 Found: C, 63.82; H, 6.33; N, 6.71.

10-(3-Hydroxypropyl)-4,9-dihydronaphtho[2,3-b]thiophen-4,9-imine (VIb):

1H NMR (CDCl$_3$, 300 MHz): 7.15-7.25 (m, 2H), 6.85-6.95 (m, 4H), 5.14 (s, 1H), 5.08 (s, 1H), 3.76 (t, J=5.3 Hz, 2H), 2.45-2.85 (two br peaks, 2H), and 1.60-1.75 (m, 2H).

IR (KBr): 3268 (br), 3068, 2934, 2912, 2872, 1454, 1416, 1372, 1088 1072, 1050, 774, and 740 cm$^{-1}$.

MS (CI, CH$_4$): 258 (100%), 212, and 199.

10-[3-(Methanesulfonyl)propyl]-4,9-dihydronaphtho[2,3-thiophen-4,9-imine (VIIb):

1H NMR (CDCl$_3$, 300 MHz): 7.20-7.25 (m, 2H), 6.90-6.95 (m, 4H), 5.09 (s, 1H), 5.03 (s, 1H), 4.30 (t, J=6.3 Hz, 2H), 2.94 (s, 3H), 2.60 (br, 2H), and 1.95-2.02 (m, 2H).

10-[3-N,N-dimethylamino)propyl]-4,9-dihydronaphtho[2,3-thiophen-4,9-imine (Ip):

1H NMR (CDCl$_3$, 300 MHz): 7.17-7.22 (m, 2H), 6.88-6.97 (m, 4H), 5.07 (s, 1H), 5.00 (s, 1H), 2.51 (br, 2H), 2.11-2.26 (m, 2H), 2.16 (s, 6H), and 1.62-1.72 (m, 2H).

IR (KBr): 3436, 3070, 2940, 2818, 2764 1454, 1100, 720, and 666 cm$^{-1}$.

MS (CI, isobutane): 285 (100%), and 184.

Conversion to the fumaric acid salt (acetonitrile/MeOH) provided 250 mg of a white solid: mp: 115° C. (dec).

1H NMR (d$_6$-DMSO, 300 MHz): 7.20-7.25 (m, 2H), 7.09-7.11 (m, 1H), 6.99 (d, J=4.5 Hz, 1H), 6.86-6.91 (m, 2H), 6.54 (s, 4H), 5.23 (s, 1H), 5.09 (s, 1H), 2.75-2.81 (m, 2H), 2.51 (s, 6H), 2.39 (br, 2H), and 1.66-1.71 (m, 2H).

IR (KBr): 3430, 3032, 2994, 2962, 2460, 1712, 1574, 1394, 1318, 1176, 978, 694, 680, and 628 cm$^{-1}$.

MS (CI, CH$_4$): 285, 117 (100%).

Analysis for $C_{17}H_{20}N_2S/2C_4H_4O_4$ Calcd: C, 58.13; H, 5.47; N, 5.43 Found: C, 58.15; H, 5.38; N, 5.47.

10-[3-(N-methylamino)propyl]-4,9-dihydronaphtho[2,3-b]thiophen-4,9-imine (Iq):

1H NMR (CDCl$_3$, 300 MHz): 7.18-7.21 (m, 2H), 6.86-6.92 (m, 4H), 5.07 (s, 1H), 5.00 (s, 1H), 2.57 (t, J=7.0 Hz, 2H), 2.30-2.60 (br, 2H), 2.36 (s, 3H), 1.63-1.73 (m, 2H), and 1.26 (br, 1H).

IR (KBr): 3424 (br), 3262, 2942, 2918, 2864, 2830, 2788 1452, 1096, 792, 740, 708, 668 $^{-1}$.

MS (CI, isobutane): 271 (100%), and 184.

Conversion to the fumaric acid salt (acetonitrile/MeOH) provided 650 mg of a yellow solid: mp: 140° C. (dec).

1H NMR (d$_6$-DMSO, 300 MHz): 7.20-7.25 (m, 2H), 7.05-7.15 (m, 1H), 6.99 (d, J=4.6 Hz, 1H), 6.87-6.91 (m, 2H), 6.44 (s, 2H), 5.22 (s, 1H), 5.09 (s, 1H), 2.83 (t, J=7.6 Hz, 2H), 2.20-2.70 (br, 2H), 2.45 (s, 3H), and 1.68-1.73 (m, 2H).

IR (KBr): 3432 (br), 3000, 2836, 2770, 2530, 2478, 1710, 1660, 1636, 1580, 1450, 1364, 1274, 1170, 794, and 638 cm$^{-1}$.

MS (CI, isobutane): 271, 117 (100%), and 89.

Analysis for $C_{16}H_{18}N_2S/C_4H_4O_4/0.2H_2O$ Calcd: C, 61.59; H, 5.79; N, 7.19; H$_2$O, 0.92 Found: C, 61.40; H, 5.46; N, 7.29; H$_2$O, 0.93.

TABLE 1

Preparation of Thieno[2,3c]pyrolles

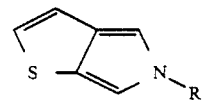

| Compound Number | R | Yield (%) | Method of Preparation[d] | Method of Purification |
|---|---|---|---|---|
| IIa | benzyl | 70 | A (24h)[e] | Recrys. (EtOH)[f] |
| IIb | cyclopropyl | 45 | A (5h) | Al$_2$O$_3$ (Hexanes)[g] |
| IIc | cyclohexyl | 80 | A (24h) | Recrys. (iPrOH) |
| IId | —CH$_3$ | —[a] | A[b] (3h) | Al$_2$O$_3$ (Ether/Pentane) |
| IIe | cyclopropylmethyl | 81 | A[c] (1h) | Al$_2$O$_3$ (Hexanes) |
| IIIa | —CH$_2$CH$_2$OH | 62 | A (4h) | Al$_2$O$_3$ (EtOH/C$_2$HCl$_2$) |
| IVa | —CH$_2$CH$_2$OSi$t$BuMe$_2$ | 49 | B | Al$_2$O$_3$ (EtOAc/Hexanes) |
| IIi | —CH(CH$_3$)$_2$ | —[a] | A (3h) | Al$_2$O$_3$ (EtOAc/Hexanes) |
| IIj | —CH$_2$CH=CH$_2$ | —[a] | A (3h) | Al$_2$O$_3$ (EtOAc/Hexanes) |
| IIk | p-methoxyphenethyl | 72 | A (4h) | Recrys. (MeOH) |
| IIn | cyclobutylmethyl | —[a] | A (3h) | Al$_2$O$_3$ (EtOAc/Hexanes) |
| IIIb | —(CH$_2$)$_3$OH | —[a] | A (4h) | Al$_2$O$_3$ (EtOAc/Hexanes) |
| IVa | —(CH$_2$)$_3$OSi$t$BuMe$_2$ | —[a] | B | Al$_2$O$_3$ (EtOAc/Hexanes) |

[a]No yield calculated. Used immediately in next reaction.
[b]10-20 eq. MeNH$_2$.
[c]Also prepared by Method C.
[d]Details of each method are included in the experimental section.
[e]stirring time.
[f]recrystallization solvent.
[g]eluting solvent for alumina column chromatography.

TABLE 2
Preparation of Naphthothiophenimines

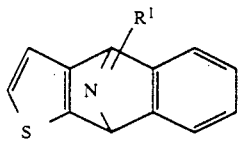

| Compound Number | R[1] | Yield (%) | Method of Preparation[c] | Purification |
|---|---|---|---|---|
| Ia | benzyl | 41 | D | SiO$_2$ (EtOAc/Hexanes)[e] then Recrys. (Hexanes)[f] |
| Ib | cyclopropyl | 72 | D | Recrys. (Hexanes) |
| Id | Me | 10 | D | SiO$_2$ (EtOAc/Hexanes) then Recrys. (EtOAc/Hexanes) |
| Ie | cyclopropylmethyl | 19 | D | SiO$_2$ (EtOAc/Hexanes) then Recrys. (EtOAc/Hexanes) |
| Ic | cyclohexyl | 45 | D | Recrys. (iPrOH) |
| Ij | allyl | 30[a] | D | SiO$_2$ (EtOAc/Hexanes) |
| Ii | isopropyl | 44[a] | D | SiO$_2$ (EtOAc/Hexanes) |
| Ik | p-methoxyphenylethyl | 8 | D | SiO$_2$ (EtOAc/Hexanes) |
| In | cyclobutylmethyl | 26[a] | D | SiO$_2$ (EtOAc/Hexanes) |
| Va | —CH$_2$CH$_2$OSitBuMe$_2$ | 55 | D | SiO$_2$ (EtOAc/Hexanes) |
| VIa | —CH$_2$CH$_2$OH | 33 | E | SiO$_2$ (EtOAc) then Recrys. (EtOAc) |
| VIIa | —CH$_2$CH$_2$OMs | b | F | none |
| Ih | —CH$_2$CH$_2$(1-PP)[d] | 53 | G | SiO$_2$ (EtOH/CH$_2$Cl$_2$) then Recrys. (CH$_3$CN) |
| Im | —CH$_2$CH$_2$NMe$_2$ | 85 | H | SiO$_2$ (EtOH/CH$_2$Cl$_2$/NH$_4$OH) |
| Ir | —(CH$_2$)$_2$NHMe | 60 | H | SiO$_2$ (CH$_2$Cl$_2$/MeOH/NH$_4$OH) |
| Io | —(CH$_2$)$_2$NEt$_2$ | 48 | H | SiO$_2$ (CH$_2$Cl$_2$/MeOH) |
| Vb | —(CH$_2$)$_3$OSitBuMe$_2$ | —[g] | D | SiO$_2$ (EtOAc/Hexanes) |
| VIb | —(CH$_2$)$_3$OH | 8[h] | G | SiO$_2$ (EtOAc) |
| VIIb | —(CH$_2$)$_3$OMs | 86 | F | none |
| Ip | —(CH$_2$)$_3$NMe$_2$ | 72 | H | none |
| Iq | —(CH$_2$)$_3$NHMe | 44 | H | SiO$_2$ (CH$_2$Cl$_2$/MeOH/NH$_4$OH) |

[a]Overall yield for two steps beginning with bromide VIII.
[b]Quantitative crude yield.
[c]Details of each method are included in the experimental section.
[d]—(CH$_2$)$_2$1-PP refers to [4-(2-pyrimidinyl)-1-piperazinyl]ethyl.
[e]elution solvent for silica gel chromatography.
[f]recrystallization solvent.
[g]no yield calculated.
[h]overall yield from compound IIIb.

Biological Testing

Compounds of the instant invention were evaluated for their ability to prevent neuronal damage caused by ischemia. As a primary screen an Anoxic Nitrogen Test in Rats was used.

In the test, the animals utilized are male Sprague-Dawley rats (200–240 grams). Animals are administered the vehicle or test compound i.p. either 30 or 60 minutes prior to the anoxic insult of exposure to 1 minute of a pure nitrogen atmosphere. This 1-minute nitrogen exposure is lethal within 3 minutes to all animals receiving only vehicle. Some animals treated with representative compounds of the present invention, however, will survive. Table 1 shows the result of the test recorded as percentage of Number of animals surviving after 2 hours Number of animals tested The foregoing results show that compounds of formula I are active in the ischemia model and thus useful in treating ischemia related disorder such as stroke.

TABLE 1

| Compound # | % survival | (dose in mg/kg) |
|---|---|---|
| Ia | 25 | (20) |
| Ib | 50 | (20) |
| Id | 13 | (20) |
| Ie | 50 | (40) |
| Ic | 50 | (20) |

TABLE 1-continued

| Compound # | % survival | (dose in mg/kg) |
|---|---|---|
| Ij | 13 | (40) |
| Ii | 13 | (40) |
| Ik | 13 | (40) |
| In | 13 | (40) |
| Ih | 13 | (20) |
| Im | 75 | (40) |
| Ir | 25 | (40) |
| Io | 33 | (40) |
| Ip | 83 | (40) |
| Iq | 33 | (40) |

What is claimed is:

1. Naphthothiophenimines of formula I or pharmaceutically acceptable acid addition salts or solvates thereof;

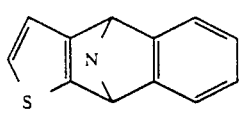

wherein R[1] is a straight or branched C$_{1-5}$ alkyl, C$_{3-5}$ alkenyl, benzyl or a radical selected from the group consisting of

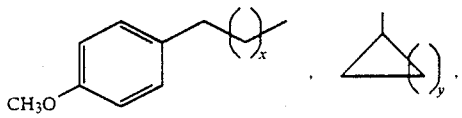

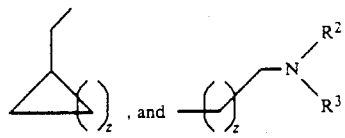

in which x is 0 to 2; y is 1, 3 or 4; z is 1 to 3; and $R^2$ and $R^3$ are independently $C_{1-3}$ alkyl, hydrogen, or $R^2$ and $R^3$ taken together constitute the radical

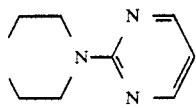

2. The compound of claim 1 wherein $R_1$ is benzyl.

3. The compound of claim 1 wherein $R_1$ is cyclopropyl.

4. The compound of claim 1 wherein $R_1$ is methyl.

5. The compound of claim 1 wherein $R_1$ is cyclohexyl.

6. The oompound of claim 1 wherein $R_1$ is allyl.

7. The compound of claim 1 wherein $R_1$ is isopropyl.

8. The compound of claim 1 wherein $R^1$ is cyclobutylmethyl.

9. The compound of claim 1 wherein $R_1$ is 3-(N,N-dimethylamino)propyl

10. The compound of claim 1 wherein $R_1$ is 2-(N,N-dimethylamino)ethyl.

11. The compound of claim 1 wherein $R_1$ is cyclopropylmethyl.

12. The compound of claim 1 wherein $R_1$ is p-methoxyphenethyl.

13. The compound of claim 1 wherein $R_1$ is 2-[4-(2-pyrimidinyl)-1-piperazinyl]ethyl.

14. The compound of claim 1 wherein $R_1$ is 2-(N-methylamino)ethyl.

15. The compound of claim 1 wherein $R_1$ is 2-(N,N-diethylamino)ethyl.

16. The compound of claim 1 wherein $R_1$ is 3-(N-methylamino)propyl. methylamino)propyl.

17. A pharmaceutical composition comprising an effective amount for treating brain ischemia and of a compound of claim 1 and a pharmaceutically acceptable carrier or diluent.

18. A method for treating brain ischemia in a mammal which comprises administering to said mammal an effective amount of a compound of claim 1.

* * * * *

UNITED STATES PATENT AND TRADEMARK OFFICE
CERTIFICATE OF CORRECTION

PATENT NO. : 5,064,831

DATED : November 12, 1991

INVENTOR(S): Katherine S. Takaki

It is certified that error appears in the above-identified patent and that said Letters Patent is hereby corrected as shown below:

Column 20,

Claim 1, formula I, that portion of the formula reading

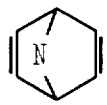

should read

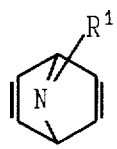

UNITED STATES PATENT AND TRADEMARK OFFICE
CERTIFICATE OF CORRECTION

PATENT NO. : 5,064,831

DATED : November 12, 1991

INVENTOR(S): Katherine S. Takaki

It is certified that error appears in the above-identified patent and that said Letters Patent is hereby corrected as shown below:

Col. 22, line 3, Claim 6, delete "oompound" should read --compound--.

Col. 22, line 8, Claim 9, add --.-- at the end of the claim.

Col. 22, line 22, Claim 16, delete "methylamino)propyl." after the first period.

Signed and Sealed this

Thirtieth Day of March, 1993

Attest:

STEPHEN G. KUNIN

Attesting Officer

Acting Commissioner of Patents and Trademarks